United States Patent
Kim et al.

(10) Patent No.: US 8,742,336 B2
(45) Date of Patent: Jun. 3, 2014

(54) BIO-CHIP FOR SECONDARY ION MASS SPECTROSCOPY AND METHOD OF FABRICATING THE SAME

(71) Applicant: Korea Research Institute of Standards and Science, Daejeon (KR)

(72) Inventors: Young-Pil Kim, Seoul (KR); Tae Geol Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 19 days.

(21) Appl. No.: 13/727,018

(22) Filed: Dec. 26, 2012

(65) Prior Publication Data
US 2013/0292561 A1    Nov. 7, 2013

(30) Foreign Application Priority Data
May 7, 2012    (KR) .................. 10-2012-0047807

(51) Int. Cl.
*H01J 49/04*    (2006.01)
(52) U.S. Cl.
CPC .................. *H01J 49/0409* (2013.01)
USPC ............. 250/288; 435/6.1; 435/7.1; 435/212; 435/219

(58) Field of Classification Search
USPC ......... 250/288, 281, 282; 435/5, 6.1, 7.1, 7.2, 435/212, 219, 174, 183
See application file for complete search history.

(56) References Cited

U.S. PATENT DOCUMENTS 7,951,572 B2 *    5/2011    Kim et al. ............. 435/219
8,323,888 B2 *    12/2012    Mirkin et al. ............. 435/6.1

FOREIGN PATENT DOCUMENTS

JP    2008-170326 A    7/2008

OTHER PUBLICATIONS

Korean Patent Office, Korean Office Action issued in corresponding KR Application No. 10-2012-0047807, dated Jul. 31, 2013.

* cited by examiner

*Primary Examiner* — Kiet T Nguyen
(74) *Attorney, Agent, or Firm* — Sughrue Mion, PLLC

(57) ABSTRACT

There are provided a bio-chip for secondary ion mass spectrometry and a method of fabricating the same, the bio-chip, which is a bio-chip for analyzing a biochemical material using the secondary ion mass spectrometry, including: a substrate; and core-shell particles positioned above substrate, wherein the core-shell particles each include a metal nanoparticle as a core and a metal shell surrounding the metal nanoparticle.

17 Claims, 5 Drawing Sheets

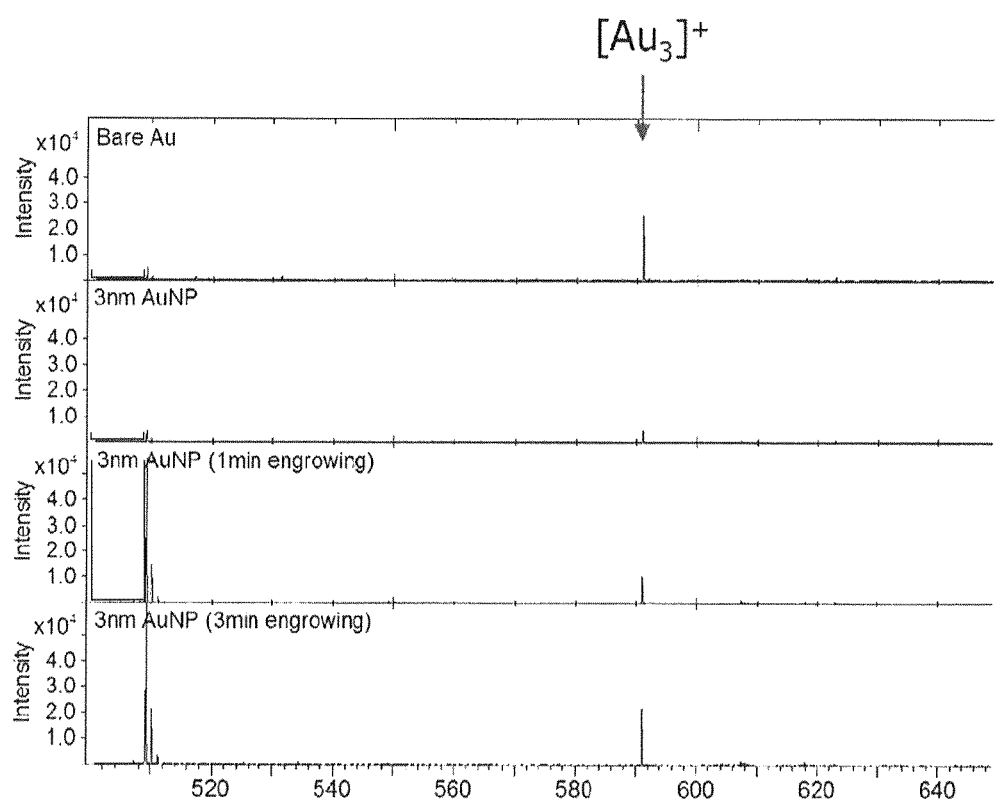

BIO-CHIP FOR SECONDARY ION MASS SPECTROSCOPY AND METHOD OF FABRICATING THE SAME

CROSS-REFERENCE TO RELATED APPLICATIONS

This application claims priority under 35 U.S.C. §119 to Korean Patent Application No. 10-2012-0047807, filed on May 7, 2012, in the Korean Intellectual Property Office, the disclosure of which is incorporated herein by reference in its entirety.

TECHNICAL FIELD

The following disclosure relates to a bio-chip for secondary ion mass spectroscopy and a method of fabricating the same, and more particularly to a bio-chip and a method of fabricating the same, capable of remarkably increasing secondary ion intensity of a biochemical material to be analyzed.

BACKGROUND

The types of mass spectrometry are an electro-spray ionization mass spectrometry and a matrix-assisted laser desorption/ionization mass spectrometry (MALDI). A surface-enhanced laser desorption/ionization (SELDI) method employing MALDI is representative as the technology of applying the mass spectrometry to the chip surface. However, in recent, secondary ion mass spectrometry (SIMS) has been known to be suitable for reproducible analysis in a low mass range since it does not use a matrix as compared with MALDI, and has been reported to be very accurate and sensitive in surface analysis at a level of several nanometers. In addition, it has been known to be very effective for quick scanning and mass analysis imaging, and thus, application thereof to analyze a biochemistry material will be expected to double the applicability thereof.

However, the secondary ion mass spectrometry has difficulty in directly analyzing a biochemical material on a chip surface due to the currently limited mass measurement range (approximately within 200 Da) thereof as compared with MALDI, and in order to overcome this, various secondary ion amplification methods have been proposed (Wu, K. J.; Odom. R. W. 1996, Anal. Chem. 68, 873-882; McArthur, S. L.; Vendettuoli, M. C., Ratner, B. D. and Castner, D. G, 2004, Langmuir 20, 3704-3709). For example, there has been introduced cationization by alkali ions or a method of increasing secondary ions through coating of the gold thin film, and recently, there is an effort to improve secondary ion efficiency using a polyatomic ion gun. In addition, U.S. Patent Laid-Open Publication No. 2008-0076676 provides a technology of using a gold nano particle as a signal amplifier. However, the above technology may have difficulties when being directly applied to bio-chips since signal improvement capability is still low and surface reproducibility is insufficient.

RELATED ART DOCUMENTS

Patent Document

U.S. Patent Laid-Open Publication No. 2008-0076676

Non-Patent Document

Wu, K. J.; Odom R. W. 1996, Anal. Chem. 68, 873-882; McArthur, S. L.; Vendettuoli, M. C., Ratner, B. D. and Castner, D. G, 2004, Langmuir 20, 3704-3709

SUMMARY

An embodiment of the present invention is directed to providing a bio-chip allowing remarkable amplification of signal at the time of secondary ion mass spectrometry, and more particularly to a bio-chip allowing remarkably more excellent amplification of signal as compared with amplification of secondary ion mass signal by gold nano particles.

In one general aspect, there is provided a bio-chip for secondary ion mass spectrometry for analyzing a biochemical material using the secondary ion mass spectrometry, the bio-chip including: a substrate; and core-shell particles positioned above substrate, wherein the core-shell particles each include a metal nanoparticle as a core and a metal shell surrounding the metal nanoparticle.

The metal shell of each of the core-shell particles may be a metal layer formed by dipping a substrate on which metal nanoparticles are positioned in a metal ion solution containing metal ions, reducing the metal ions, and inducing nucleation and growth using the metal nanoparticles as a seed.

The core-shell particles may satisfy Relational Formula 1 below:

$$SCnp < SCcs < 1 \qquad \text{(Relational Formula 1)}$$

(In Relational Formula 1, SCnp is surface coverage of metal nanoparticles on a surface of the substrate and means area of the substrate covered with the metal nanoparticles per unit surface area of the substrate; and SCcs is surface coverage of core-shell particles on the surface of the substrate and means area of the substrate covered with the core-shell particles per unit surface area of the substrate).

The substrate may be a composite substrate having a self-assembled monolayer formed on the surface of the substrate, and the metal nanoparticles are bonded with terminal groups of the self-assembled monolayer to thereby be immobilized onto the substrate.

The substrate and the core-shell particle may be surface-contacted with each other by the metal shell of the core-shell particle.

The biochemical material as an analyte for mass spectrometry may be bonded to the core-shell particle.

Here, a metal of the metal nanoparticle may be Au or Ag, and a metal of the metal shell may be Au or Ag.

In another general aspect, there is provided a method of fabricating a bio-chip for secondary ion mass spectrometry for analyzing a biochemical material using the secondary ion mass spectrometry, the method including: positioning metal nanoparticles above a substrate; and forming core-shell particles each consisting of the metal nanoparticle as a core and a metal shell, by growing the metal shell, which is a metal layer surrounding a surface of the metal nanoparticle, using the metal nanoparticle as a seed through a liquid phase reduction method.

In the method, step a) may include: a1) forming a self-assembled monolayer on a surface of the substrate; and a2) coating a dispersion liquid containing the metal nanoparticles on the substrate having the self-assembled monolayer formed thereon, to thereby bond terminal groups of the self-assembled monolayer and the metal nanoparticles with each other.

In the method, step b) may be performed by dipping the substrate on which the metal nanoparticles are positioned in a mixture solution containing metal ions and a reducing agent.

In the method, step b) may include: b1) dipping the substrate on which the metal nanoparticles are position in a metal ion solution containing metal ions; and b2) feeding a reducing agent into the metal ion solution to reduce the metal ions, to thereby form the metal shell as the metal layer surrounding the metal nanoparticle.

The reducing agent may be hydroxylamine hydrochloride, cetyltrimethylammonium bromide, nicotinamide adenine dinucleotide, or a mixture thereof.

Here, a size of the core-shell particle, a shape of the core-shell particle, and a distance between the core-shell particles may be controlled by the time period while reducing in step b) is performed.

In the method, at the time of the liquid phase reduction method, the molar concentration of metal ions in a liquid containing a metal ion solution may be 0.1 to 10 mM, and a reducing agent reducing the metal ions may be fed to have a molar concentration of 0.1 to 10 mM in the liquid.

The method may further include, after step b), c) coating an analysis solution containing the biochemical material on a surface of the substrate on which the core-shell particles are formed, to thereby bond the biochemical material to the core-shell particles.

The molar concentration of the biochemical material in the analysis solution may be 0.01 to 100M.

In still another general aspect, there is provided a mass spectrometry method of a biochemical material for analyzing secondary ion mass of the biochemical material by using the bio-chip as described above and secondary ion mass spectrometry.

BRIEF DESCRIPTION OF THE DRAWINGS

FIG. 4A to 4D show secondary ion mass spectrometry spectra measurement results with respect to substrates to which peptide containing a thiol group is bonded.

DETAILED DESCRIPTION OF EMBODIMENTS

Figure 1:
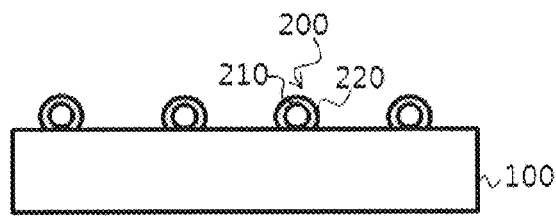
FIG. 1 is a cross sectional view of a bio-chip according to an exemplary embodiment of the present invention.

Hereinafter, a bio-chip and a method of fabricating the same of the present invention will be described in detail with reference to the accompanying drawings. The drawings exemplified below are provided by way of examples so that the spirit of the present invention can be sufficiently transferred to those skilled in the art to which the present invention pertains. Therefore, the prevent invention is not limited to the drawings set forth below, and may be embodied in different forms, and the drawings set forth below may be exaggerated in order to clarify the spirit of the present invention. Here, unless indicated otherwise, the terms used in the specification including technical and scientific terms have the same meaning as those that are usually understood by those skilled in the art to which the present invention pertains, and detailed description of the known functions and constitutions that may obscure the gist of the present invention will be omitted.

The present applicants put in a great deal of effort in order to enhance secondary ion intensity of a biochemical material, and then found that the coverage of metal particles, which function as an amplifier, on the surface of the substrate, had a very remarkable effect on enhancing secondary ion intensity, and as a result of the above, the present application has been filed.

The present invention is directed to a bio-chip for secondary ion mass spectrometry for analyzing a biochemical material without label, using the secondary ion mass spectrometry, the bio-chip including: a substrate; and core-shell particles positioned over the substrate. The core-shell particles each include a metal nano-particle as a core, and a metal shell surrounding the metal nanoparticle.

In the present invention, the bio-chip may include a peptide chip. In the present invention, the bio-chip may be used together with a secondary ion mass spectrometer (second ion mass spectrometry). In the present invention, the secondary ion mass spectrometer (or secondary ion mass spectrometry) may include a time-of-flight secondary ion mass spectrometer (or time-of-flight secondary ion mass spectrometry).

In the bio-chip according to an embodiment of the present invention, the metal shell of each of the core-shell particles may be a metal layer formed by dipping a substrate on which the metal nanoparticles are positioned in a metal ion solution containing metal ions, reducing the metal ions, and inducing nucleation and growth by using each of the metal nanoparticle as a seed.

When the metal nanoparticles are positioned on the substrate, metal nanoparticle density on the surface of the substrate is reduced due to electrostatic repulsive force between the metal nanoparticles, and further the metal nanoparticles previously positioned on the substrate disturb smooth adsorption of other metal nanoparticles, and thus, there are limits in increasing metal nanoparticle density on the surface of the substrate and coverage of the metal nanoparticles on the surface of the substrate.

The bio-chip according to an embodiment of the present invention has an advantage of having remarkably amplified secondary ion intensity of a biochemical material, by positioning the metal nanoparticles on the substrate, and then forming the metal shell, which is a metal layer covering the surface of the metal nanoparticle, by using each of the metal nanoparticles as a seed.

In addition, the bio-chip according to an embodiment of the present invention can obtain remarkably more enhanced secondary ion intensity than a bio-chip including metal nanoparticles or a metal thin film, by positioning the metal nanoparticles on the substrate, and then forming the metal shell, which is a metal layer covering the surface of the metal nanoparticle, by using each of the metal nanoparticles as a seed through a liquid phase reduction method.

In the bio-chip according to an embodiment of the present invention, the metal nanoparticle may include a metal nanoparticle surface-modified with ligand. Specifically, the metal nanoparticle may include a metal nanoparticle stabilized by ligand, and the ligand may be one or two or more selected from the group consisting of citrate, n-alkanethiol, PEG-thiol (polyethyleneglycol thiol), dendrimer, alkylphosphine, alkylphosphine oxide, sulfur-containing ligands(H2S, (trimethylsilyl)$_2$S, xanthate, disulfide, dithiol, trithiol, resorcinarene tetrathiol), (trimethylsilyl)$_3$P, aryl isocyanine, acetone, iodine, PEG, and starch.

In the bio-chip according to an embodiment of the present invention, the substrate functions as a support. The substrate may include a metal, a metal compound containing metal oxide, a semiconductor, a semiconductor compound containing semiconductor oxide or semiconductor nitride, plastic, or a laminate thereof, and may be in a plate type. The substrate may be a nonconductor, and the substrate may be crystalline or non-crystalline. Substantial examples thereof may include glass; silicon; Au, Ag, Pd, Pt, Cu, Zn, Fe, In, or metal oxides thereof; $Fe_2O_3$, $SiO_2$, or indium tin oxide (ITO).

In the bio-chip according to an embodiment of the present invention, the substrate is a composite substrate having a self-assembled monolayer (SAM) formed on the surface of the substrate. The self-assembled monolayer is an organic monolayer self-assembled on the surface of the substrate, and an organic monomer of the organic monolayer may include a reactive group at a head portion thereof, which is bonded to the substrate; an alkane chain in a body portion thereof, which enables regular formation of the monolayer; and a functional group at a terminal portion thereof. In addition, the organic monomer may further include a moiety selected the group consisting of ethylene glycol (—O—$CH_2$—$CH_2$—), carboxylic acid (—COOH), alcohol (—OH), ether (—O—), ester (—COO—), ketone (—CO—), aldehyde (—COH), amide (—NH—CO—), and aromatic group substitutions thereof (for example, phenol.

The simplest example of the functional group at the terminal portion may be an alkyl group, and further examples thereof may include at least one group selected from an alkane group, an alcohol group, an amine group, a thiol group, a carboxyl group, an aldehyde group, an epoxy group, and a maleimide group.

As the reactive group at the head portion, any reactive group that can be spontaneously bonded to a surface atom constituting the surface of the substrate to thereby enable self-assembly is enough. The reactive group may be appropriately designed in consideration of a material of the substrate. For example, the reactive group may be a thiol group or a silane group enabling spontaneous bonding with the substrate via sulfur or silicon.

More specifically, the self-assembled monolayer may be prepared by using alkanoic acid forming ionic bonds with the substrate, an organosulfur compound forming charge-transfer complexes with the substrate, or an organosilicon compound forming pure covalent bonds with the substrate. Specific examples of the compound forming the self-assembled monolayer may include n-alkanoic acid ($C_nH_{2n+1}COOH$); alkyl silanes, such as alkylchlorosilanes, alkylalkoxysilanes or alkylaminosilanes; and organosulfur compounds, such as alkylthiolates, n-alkyl sulfide, di-n-alkyl disulfide, thiophenols, mercaptopyridines, mercaptoanilines, or mercaptoimidazoles. Here, the compounds each may have 3~25 carbon atoms.

In the bio-chip according to an embodiment of the present invention, the metal nanoparticles may be bonded and immobilized to the substrate. Specifically, the metal nanoparticles may be bonded and immobilized onto the substrate through ionic bonding, covalent bonding, or bonding between the metal nanoparticle and the functional group of the substrate. More specifically, the metal nanoparticle may include a metal nanoparticle surface-modified with ligand, and the substrate may be a composite substrate having a self-assembled monolayer formed on the surface thereof. The metal nanoparticle may be immobilized and positioned onto the substrate by chemical bonding between the ligand present on the surface thereof and the functional group of the self-assembled monolayer.

In the bio-chip according to an embodiment of the present invention, an example of a biochemical material, which is an analyte for mass spectrometry, may include polymer organic materials, organometal compounds, peptides, carbohydrates, proteins, lipids, metabolites, antigens, antibodies, enzymes, amino acids, aptamers, sugar, nucleic acids, and mixtures thereof.

Here, the polymer organic materials, organometal compounds, peptides, carbohydrates, proteins, lipids, metabolites, antigens, antibodies, enzymes, amino acids, aptamers, sugar, nucleic acids, and mixtures thereof, which are the analytes for mass spectrometry, may be in a state before or after specific reaction treatment with a chemical or biochemical material.

In the bio-chip according to an embodiment of the present invention, the biochemical material may be immobilized to the core-shell particle. The immobilizing of the biochemical material may be varied depending on the aspects of the core-shell particle and the biochemical material, and may be achieved by, for example, physical adsorption, covalent bonding, ionic bonding, hydrophobic bonding, or thiol adsorption. Specifically, when the biochemical material is peptide, the immobilizing thereof may be achieved by ionic bonding between a metal of the metal shell and an amine group of the peptide, or the immobilizing thereof may be achieved by thiol adsorption using cysteine of the peptide.

FIG. 1 is a cross sectional view of a bio-chip according to an embodiment of the present invention. As shown in FIG. 1, the bio-chip according to an embodiment of the present invention may include a substrate 100; and core-shell particles 200 each consisting of a metal nano-particle 210 as a core and a metal shell 220 surrounding the metal nano particle. The core-shell particle 200 may be prepared by using a liquid phase reduction method targeting the metal nanoparticle 210 positioned on the substrate 100 to thereby form the metal shell 220 surrounding the metal nanoparticle 210. Metal ions contained in a liquid are reduced by the liquid phase reduction method, and nucleation and growth using the metal nanoparticle 210 as a seed are induced, thereby forming the metal shell 220, which is a metal layer covering a surface of the metal nanoparticle 210. That is, the metal shell 220 of each of the core-shell particles 200 may be a metal layer formed by dipping the substrate 100 on which the metal nanoparticles 210 are positioned in a metal ion solution containing metal ions, reducing the metal ions, and inducing nucleation and growth by using each of the metal nanoparticles 210 as a seed.

The liquid phase reduction method may include a method of adding a reducing agent to the metal ion solution containing the metal ions and reducing the metal ions to form a metal (hereinafter, referred to as "a reduced metal"). Here, the metal ions contained in the metal ion solution, of course, include ions of metals constituting the metal shell 220 to be formed.

The meaning that the metal ions contained in a liquid are reduced by the liquid phase reduction method and the reduced metals are nucleated and grown using the metal nanoparticle 210 as a seed is that heterogeneous nucleation of the reduced metals using a surface of the metal nanoparticle 210 as a nucleation site is induced and the reduced metal nuclei are grown.

The heterogeneous nucleation may multiply and simultaneously occur in the entire region of the surface of the metal nanoparticle functioning as a seed, and of curse, other reduced metal nuclei may be generated at the same time while the growing of the generated nuclei occurs.

As described above, in the bio-chip according to an embodiment of the present invention, the metal nanoparticle is loaded on the substrate and then the liquid phase reduction method using the loaded metal nanoparticle as a nucleation site is employed, to thereby form the metal layer surrounding the surface of the metal nanoparticle. Therefore, the size of the metal particle (core-shell particle), the shape of the metal particle (core-shell particle), and the distance between the metal particles (core-shell particles) can be controlled, and the coverage on the surface of the substrate covered with the metal particles (core-shell particles) can be significantly improved.

In the bio-chip according to an embodiment of the present invention, the core-shell particle may satisfy Relational Formula 1 below:

$$SCnp < SCcs < 1 \quad \text{[Relational Formula 1]}$$

In Relational Formula 1, SCnp is surface coverage of metal nanoparticles on a surface of the substrate and means area of the substrate covered with the metal nanoparticles per unit surface area of the substrate; and SCcs is surface coverage of core-shell particles on the surface of the substrate and means area of the substrate covered with the core-shell particles per unit surface area of the substrate.

In the bio-chip according to an embodiment of the present invention, the core-shell particle, preferably, may satisfy Relational Formula 2 below:

$$2 \times SCnp \leq SCcs \leq 0.98 \quad \text{[Relational Formula 2]}$$

By forming the metal shells such that the core shell particles satisfy Relational Formula 2 above, the present invention can have 25 times as much or higher the effect of enhancing secondary ion intensity as compared with a substrate on which only nanoparticles are provided.

In order to reduce electrostatic repulsive force between the metal nanoparticles and form the metal nanoparticles on the substrate in a uniform distribution, the size of the metal nanoparticle may be 1 to 50 nm, and the value of SCnp may substantially be 0.1 to 0.25 in Relational Formulas 1 and 2 above.

That is, the metal shells may be formed such that they satisfy Relational Formula 1 above, preferably Relational Formula 2 above. Specifically, the metal shells may be formed such that they satisfy Relational Formula 1 above, preferably Relational Formula 2 above, by controlling the concentration of the metal ion solution for forming the metal shells, the feeding amount of the reducing agent, and/or the time period while reducing of the metal ions are performed.

For example, the molar concentration of the metal ions in the metal ion solution for forming the metal shells may be 0.1 to 10 mM, and the reducing agent for reducing the metal ions may be fed to have a molar concentration of 0.1 to 10 mM in the metal ion solution. The reducing agent may be hydroxylamine hydrochloride, cetyltrimethylammonium bromide, nicotinamide adenine dinucleotide, or a mixture thereof. The reducing of the metal ions may be performed for 30 seconds to 5 minutes, based on the molar concentration of the metal ions of the metal ion solution, the feeding amount of the reducing agent, and the kind of reducing agent, and thus, the metal shells satisfying Relational Formula 1, preferably Relational Formula 2 can be formed.

As described above, in the bio-chip according to an embodiment of the present invention, the metal shell of the core-shell particle may be a metal layer surrounding the surface of the metal nanoparticle, which is formed by dipping the substrate on which the metal nanoparticle is formed in a metal ion solution containing metal ions and reducing the metal ions. Here, the substrate on which the metal nanoparticle is formed may mean a substrate on which the metal nanoparticle is positioned and/or a substrate to which the metal nanoparticle is bonded.

Figure 2:
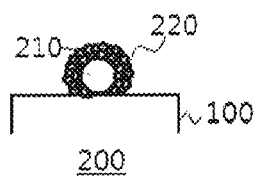
FIG. 2 is a view showing a core-shell particle in more detail in the bio-chip according to the exemplary embodiment of the present invention.

FIG. 2 is a view showing the core-shell particle 200 in more detail, in the bio-chip according to the embodiment of the present invention. As shown in FIG. 2, the nucleation and growth of the reduced metals using the metal nanoparticle 210 as a seed by a liquid phase reduction method are induced, and thus, the surface of the metal shell 220, which is a surface of the core-shell particle 200, consists of particles formed by growing a plurality of nuclei of reduced metal.

In order to uniformly and stably distribute the metal nanoparticles amplifying the secondary ion intensity on the substrate, a dispersion liquid where metal nanoparticles are dispersed in a colloidal type may be coated on the substrate on which the self-assembled monolayer enabling bonding with the metal nanoparticles is formed.

However, when the metal nanoparticles are immobilized onto the surface of the substrate by using the self-assembled monolayer, the metal nanoparticles are immobilized onto the substrate by using self-assembled monomers as linkers, which may cause physical and chemical stability of the bio-chip to be reduced.

In the bio-chip according to an embodiment of the present invention, the core-shell particles are formed by impregnating the substrate on which the metal nanoparticles are positioned with a solution containing the metal ions and reducing the metal ions, to thereby form the metal shells surrounding the metal nanoparticles, respectively, and thus, the substrate and the core-shell particles are surface-contacted with each other to form physical interfaces therebetween by the metal shells. Hence, the intensity of the secondary ion mass signal can be enhanced and physical and chemical stability of the bio-chip can be improved.

In addition, as nucleation and growth of the reduced metal are multiply and simultaneously induced on the surface of the metal nanoparticle by the liquid phase reduction method, surface roughness thereof is increased, and thus, high-quality bonding sites with the biochemical material as an analyte for mass spectrometry can be provided in a large amount.

In the bio-chip according to an embodiment of the present invention, the metal of the metal nanoparticle may be Au or Ag, and the metal (metal ions contained in the solution) of the metal shell may be Au or Ag, independently from the metal nanoparticle.

In the bio-chip according to an embodiment of the present invention, as described above, the metal nanoparticles each may have a size of 1 to 50 nm, so that the metal nanoparticles minimize electrostatic repulsive force therebetween and are positioned on the substrate in a uniform distribution. The size of the core-shell particle where the metal shell is formed on the metal nanoparticle may be controlled by the thickness of the metal shell, which is formed so as to satisfy Relational Formula 1 above, preferably Relational Formula 2 above. The shape of the core-shell particle may be varied depending on the reducing conditions or the reducing time of the metal ions for forming the metal shell, but may be macroscopically a hemispherical shape, or a cylindrical shape of which one end is hemispherical. The distance between the core-shell particles is the shortest distance between surfaces of the nearest adjoining core-shell particles based on the surfaces of the core-shell particles. The distance between the core-shell particles may be controlled by the thickness of the metal shell formed so as to satisfy Relational Formula 1 above, preferably Relational Formula 2, and may be controlled up to, for example, 1 nm to 100 nm.

The present invention provides a method of fabricating a bio-chip for secondary ion mass spectrometry for analyzing a biochemical material by using secondary ion mass spectrometry. In the present invention, the secondary ion mass spectrometry includes time-of-flight secondary ion mass spectrometry.

A method of fabricating a bio-chip for secondary ion mass spectrometry according to the present invention includes: a) positioning metal nanoparticles on a substrate; and b) forming core-shell particles each consisting of the metal nanoparticle as a core and a metal shell, by growing the metal shell, which is a metal layer surrounding a surface of the metal nanoparticle, using the metal nanoparticle as a seed through a liquid phase reduction method.

In the method of fabricating a bio-chip for secondary ion mass spectrometry according to the present invention, step a) may include a1) forming a self-assembled monolayer on a surface of the substrate; and a2) coating a dispersion liquid containing the metal nanoparticles on the substrate on which the self-assembled monolayer is formed, to thereby bond terminal groups of the self-assembled monolayer and the metal nanoparticles with each other.

Step a1) may be performed by using the conventionally known method. For example, the self-assembled monolayer may be formed by employing the technology disclosed in Jing Li etc., Langmuir (2007), vol. 23, pp. 11826-11835 and Benjamin etc., Langmuir (2003), vol. 19, pp. 1522-1531. For example, step a1) may be performed by impregnating the substrate with a monomer solution containing 2 mM to 10 mM of organic monomers for forming the self-assembled monolayer. The impregnating may be performed at room temperature for 2 to 24 hours, and may be performed at a temperature of 30 to 40° C. in order to form the self-assembled monolayer more promptly. Here, before the forming of the self-assembled monolayer, cleaning for removing an oxide film or impurities on the surface of the substrate may be performed, and of course, step a1) may be performed in an inert atmosphere containing nitrogen.

A metal of the metal nanoparticle in step a2) may be Au or Ag, and the metal nanoparticle in step a2) may include a metal nanoparticle surface-modified with ligand. The metal nanoparticles stabilized by the ligands may be manufactured by utilizing the conventionally known method (Handley, D. E. In Colloidal Gold-Principles, Method, and Applications; Hayat, M. A., Ed.; Academic Press: New York, 1989; Vol 1, Chapter 2, 13-32).

Step a2) may be performed by coating a dispersion liquid where the metal nanoparticles are homogeneously dispersed on the substrate on which the self-assembled monolayer is formed. Specifically, the metal nanoparticle dispersion liquid may be coated on a surface of the self-assembled monolayer; the self-assembled monolayer may be impregnated with the metal nanoparticle dispersion liquid; or the metal nanoparticle dispersion liquid may be flowed onto the surface of the self-assembled monolayer at a constant flow rate. For substantial example, the reaction between self-assembled monolayer and the metal nanoparticle dispersion liquid may be performed at room temperature for 30 minutes or at 4° C. for 1~2 hours, for bonding between the metal nanoparticles and the functional groups of the self-assembled monolayer, and then the surface of the self-assembled monolayer may be washed to remove non-bonded metal nanoparticles. As the reaction time at room temperature takes longer, agglomeration may occur in the metal nanoparticle dispersion liquid, and thus, it is preferable to avoid performing reaction 1 hour or longer.

In the method of fabricating a bio-chip for secondary ion mass spectrometry according to an embodiment of the present invention, step b) may include b1) dipping the substrate on which the metal nanoparticles are position in a metal ion solution containing metal ions; and b2) feeding a reducing agent into the metal ion solution to reduce the metal ions, to thereby form the metal shell as the metal layer surrounding the metal nanoparticle.

The metal ion in step b1) may be Au ion or Ag ion, independently from the metal of the metal nanoparticle. Step b1) may be performed by dipping the substrate on which the metal nanoparticles are positioned in a metal ion solution, or coating the metal ion solution on the substrate so that all the metal nanoparticles are at least submerged. The molar concentration of the metal ions in the metal ion solution may be 0.1 to 10 mM.

As described above, after the submerging in step b1) is performed, the reducing agent is fed into the solution in which the substrate is dipped in step b2}, to thereby reduce the metal ions in the metal ion solution, thereby forming metal nanoparticle type metal shells. Here, the reducing agent for reducing the metal ions may be fed to have a molar concentration of 0.1 to 10 mM in the metal ion solution. The reducing agent may be hydroxylamine hydrochloride, cetyltrimethylammonium bromide, nicotinamide adenine dinucleotide, or a mixture thereof.

Steps b1) and b2) may be performed at room temperature, and the reducing time of the metal ions may be controlled by the dipping time of the substrate, that is, the time period directly from when the substrate is dipped in the solution to when the substrate is separated and collected from the solution. The reducing time may be 30 seconds to 5 minutes.

For modification example of the fabricating method of the present invention, of course, in step b), the substrate may be dipped in the metal ion solution directly after the reducing agent is fed into the metal ion solution.

That is, in the method of fabricating a bio-chip for secondary ion mass spectrometry according to an embodiment of the present invention, step b) may be performed by dipping the substrate in a mixture solution containing the metal ions and the reducing agent.

Here, as described above, the mixture solution may contain 0.1 to 10 mM of metal ions, and may contain a reducing agent in a molar concentration of 0.1 to 10 mM. The reducing by the mixture solution may be performed at room temperature and the reducing time may be 30 seconds to 5 minutes.

In step b), the method of feeding the reducing agent into the metal ion solution after the substrate on which the metal nanoparticles are positioned is dipped in the metal ion solution (Method 1) may be in danger of decreasing the uniform reducing power in the liquid but improve the heterogeneous nucleation efficiency, and the method of dipping the substrate on which the metal nanoparticles are positioned in the mixture solution containing both the metal ions and the reducing agent (Method 2) may provide the uniform reducing power in the liquid but be in danger of generating particles of the reduced metal due to homogeneous nucleation. In the case of Method 1, it is preferable to minimize non-uniform reducing power by feeding a dissolved state of the reducing agent, and in the case of Method 2, it is preferable to minimize the possibility of uniform nucleation by containing 0.1 to 10 mM of metal ions and 0.1 to 10 mM of the reducing agent in the mixture solution.

The size of the core-shell particle, the shape of the core-shell particle, and/or the distance between the core-shell particles may be controlled by the time period while the reducing of step b) is performed.

For substantial example, the core-shell particle satisfying Relational Formula 1, preferably Relational Formula 2 may be prepared by using a metal ion solution containing 0.1 to 10 mM of metal ions, feeding the reducing agent, which is selected from hydroxylamine hydrochloride, cetyltrimethylammonium bromide, nicotinamide adenine dinucleotide, or a mixture thereof, to the metal ion solution such that the reducing agent has a molar concentration of 0.1 to 10 mM, and reducing the metal ions at room temperature for 30 seconds to 5 minutes.

However, the conditions for forming the metal shell satisfying Relational Formula 1, preferably Relational Formula 2 may be, of course, appropriately varied depending on the molar concentration of the metal ions, the kind of reducing agent, the feeding amount of the reducing agent, the temperature at which the reducing is performed, and the reducing time.

After step b) is performed, washing of the substrate separated and collected from the metal ion solution (or mixture solution) may be further performed, and this washing may be performed by using deionized water.

The method of fabricating a bio-chip for secondary ion mass spectrometry according to an embodiment of the present invention may further include, after the core-shell particles are formed on the substrate by step b), c) coating an analysis solution containing the biochemical material on a surface of the substrate on which the core-shell particles are formed, to thereby bond the biochemical material to the core-shell particles.

The molar concentration of the biochemical material in the analysis solution may be 0.01 to 100M. As the liquid for the analysis solution containing the biochemical material, any liquid in a stable state that fails to induce chemical reaction with the biochemical material to be analyzed may be used. For example, as the liquid for the analysis solution, a hydrophilic solvent such as, pure distilled water or a buffer solution (PBS, HEPES, Tris buffer, etc.), or an organic solvent, such as, dimethylsulfoxide (DMSO), ethanol, or the like, may be used. For substantial example, in the case where peptide is an analyte material, the liquid for the analysis solution may be 10~100 mM of PBS or HEPES solution in a neutral pH (6~7) state.

In order to bond the biochemical material to the core-shell particles, the substrate on which the core-shell particles are formed may be dipped in the analysis solution at 4° C. to room temperature for 0.5 to 2 hours.

The present invention provides a mass spectrometry method of a biochemical material for analyzing secondary ion mass of the biochemical material by using the above-described bio-chip and secondary ion mass spectrometry. In the present invention, the secondary ion mass spectrometry includes time-of-flight secondary ion mass spectrometry.

The mass spectrometry method according to the present invention has remarkably enhanced secondary ion intensity, and thus, can significantly improve accuracy in detection, and detect an infinitesimal amount of biochemical material due to significantly excellent signal to noise ratio (SNR). Also, the mass spectrometry method according to the present invention can sensitively and accurately detect a biochemical material having a very large mass, and achieve more stable and reproducible analysis.

Hereinafter, the present invention will be described in more detail with reference to an example. However, the following example is merely provided in order to help more overall comprehension of the present invention, but do not intend to limit the scope of the present invention. Therefore, the spirit of the present invention should not be limited to the above-described exemplary embodiments, and the following claims as well as all modified equally or equivalently to the claims are intended to fall within the scope and spirit of the invention.

Example

A 10 mm×10 mm cut Si wafer (hereinafter, Si substrate) was used as the substrate. The Si substrate was immersed in a pirana solution of sulfuric acid/hydrogen peroxide for 20 minutes, and then taken out of the solution, followed by washing with distilled water and methanol.

The washed Si substrate was immersed in a methanol solution containing 3-aminopropyl-trimethoxysilane (PTMS) (Sigma-Aldrich) dissolved therein, for 12 hours, and then taken out of the solution, followed by washing with methanol, thereby manufacturing a Si substrate on which a self-assembled monolayer was formed.

0.1 g of $HAuCl_4.3H_2O$ (Sigma-Aldrich, 99.9%) was added to 100 mL of pure distilled water, followed by stirring for 1 minute, and then 0.02 g of sodium citrate dehydrate (2-hydroxy-1,2,3-propanetricarboxylic acid, Sigma-Aldrich) was added thereto, followed by again stirring for 1 minute After stirring was completed, 85 μL of a stock solution where 11.4 mg of $NaBH_4$(Sodium borohydride, Sigma-Aldrich) was dissolved in 1 mL of deionized water was added to the above solution, and then, the mixture solution was additively stirred at room temperature for 10 minutes, thereby preparing a dispersion liquid of gold nanoparticles surface-modified with citrate. Then, the prepared dispersion liquid was stored at 4° C. before the use thereof.

As the observed result of the prepared gold nanoparticles using an energy-filtering transmission electron microscopy (EF-TEM, EM912 Omega, Carl Zeiss, Germany), the average particle size thereof was 3.2 nm (S.D.=±0.4 nm).

The Si substrate having the self-assembled monolayer formed thereon was immersed in the prepared dispersion liquid of gold nanoparticles for 2 hours, followed by washing with distilled water, thereby manufacturing a Si substrate to which gold nanoparticles were bonded.

The manufactured Si substrate onto which gold nanoparticles were bonded was impregnated with 1 mL of distilled water containing 0.3 mM of $HAuCl_4.3H_2O$ and 0.4 mM of hydroxylamine hydrochloride (Sigma-Aldrich, 99%) for 1 minute or 3 minutes, and then the substrate was taken out of the solution, followed by washing with distilled water, thereby manufacturing a Si substrate to which core-shell particles were formed. Hereinafter, a substrate on which core shell particles are formed by performing reducing for 1 minute will be referred to as a "first core-shell particle substrate", and a substrate on which core shell particles are formed by performing reducing for 3 minutes will be referred to as a "second core-shell particle substrate.

In addition, for characterization comparison, a Si substrate on which only gold nanoparticles are positioned instead the core-shell particles will be referred to as a "nanoparticle substrate", and a substrate in which gold is provided in a thin film type but not a particle type, that is, a substrate on which a gold thin film is coated on a Si wafer will be referred to as a "thin film substrate".

Figure 3:
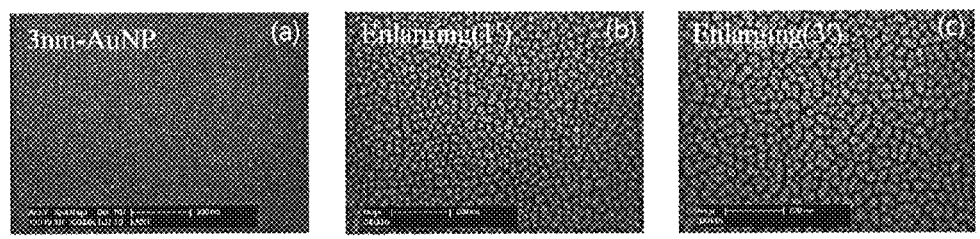
FIG. 3 shows a scanning electron microscopy (SEM) image of a nano-particle substrate, which is a Si substrate onto which gold nano-particles are attached ((a) of FIG. 3), an SEM image of a first core-shell particle substrate, which is a Si substrate on which core-shell particles are formed, the core-shell particles being prepared by performing reducing for 1 minute ((b) of FIG. 3), and an SEM image of a second core-shell particle substrate, which is a Si substrate on which core-shell particles are formed, the core-sell particles being prepared by performing reducing for 3 minutes are attached ((c) of FIG. 3).

FIG. 3 shows an SEM image of a nano-particle substrate as a Si substrate onto which gold nano-particles are attached ((a) of FIG. 3), an SEM image of a first core-shell particle substrate as a Si substrate onto which core-shell particles formed by performing reducing for 1 minute are attached ((b) of FIG. 3), and an SEM image of a second core-shell particle substrate as a Si substrate onto which core-shell particles formed by performing reducing for 3 minutes are attached ((c) of FIG. 3).

It can be seen from (a) of FIG. 3 that gold nanoparticles having a negative charge were attached to a substrate having a positive charge by an amino group in a monolayer type by electrostatic attraction, but the distance between the gold nanoparticles was very large due to electrostatic repulsive force between the gold nanoparticles, and thus, the gold nanoparticles were not densely positioned on the substrate.

It can be seen from (b) and (c) of FIG. 3 that, in the case where gold (Au) shells are formed on gold nanoparticles by using a liquid phase reduction method, a decrease in surface coverage due to electrostatic repulsive force can be changed to an increase in surface coverage by using the gold shells.

Specifically, it can be seen based on scanning electron microscope images that, as the calculated result of surface coverage of the gold nanoparticles or the core-shell particles covering the surface of the substrate per unit area of the substrate, in the case where only gold nanoparticles were formed, the coverage thereof was only 18%, and in the case where core-shell particles were formed, the surface coverage thereof was 77% for the first core-shell particle substrate and 95% for the second core-shell particle substrate.

In addition, it can be seen that, as heterogeneous nucleation and growth using a gold nanoparticle as a seed occurred, individual core-shell particles were not agglomerated to each other and particle shapes independently separated from each other were maintained.

An aqueous peptide solution containing peptide Ac-IYAAPKKGGGGC (Mr=1162.58, Cysteine-tethered Abl peptide) (Peptron Co., Ltd., Korea) in a molar concentration of 0.01, 0.1, 1, or 100M was used to bond the peptide to the manufactured substrate (a first core-shell particle substrate, a second core-shell particle substrate, a nanoparticle substrate, or a thin film substrate). Specifically, the manufactured substrate was immersed in the aqueous peptide solution for 60 minutes, and taken out of the solution, followed by washing with distilled water, and then dried using a nitrogen gas, thereby manufacturing a substrate to which a biochemical material is bonded.

For secondary ion mass spectrometry, time-of-flight secondary ion mass spectroscopy (TOF-SIMS) was used. As the measurement conditions of TOF-SIMS, TOF-SIMS V (ION-TOF GmbH, Germany) equipped with a Bi ion gun was used. The 25 keV $Bi_1^+$ ion gun was used, and the ion amount measured by using a Faraday cup positioned on a grounded sample holder was 0.5 pA at 5 kHz. It was operated at a pulse of 0.1 ns, and the mass resolving power (M/ΔM) at secondary ion mass (m/z)>500 was 10000 or higher in both a positive mode and a negative mode. The measurement region was 500×500 μm$^2$, and the ion amount was maintained at 1012 ions cm-2 or less in order to satisfy static SIMS conditions. The cation spectra were calibrated by using $H^+$, $H_2^+$, $CH_3^+$, $C_2H_3^+$ and $C_3H_4^+$ peaks as a reference, and thus, accurate masses with respect to peaks were obtained. In addition, the intensities of all peaks in the secondary ion mass spectrometry spectra obtained through measurement in the present example were normalized to a total intensity where all the intensities of the peaks in the spectra are accumulated.

Figure 4B:
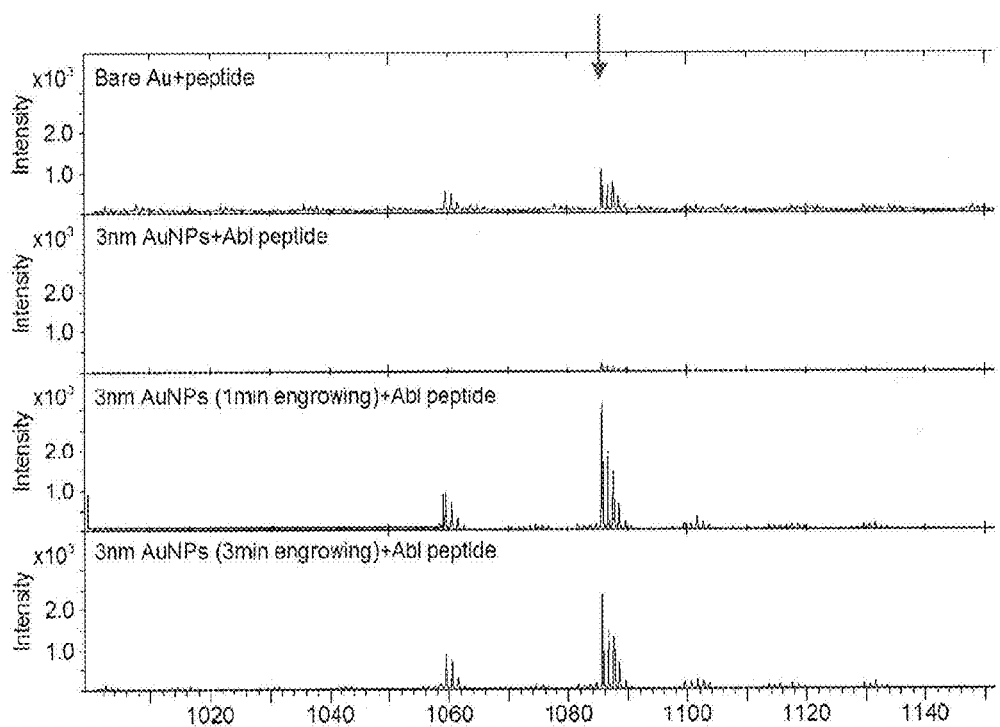
Figure 4C:
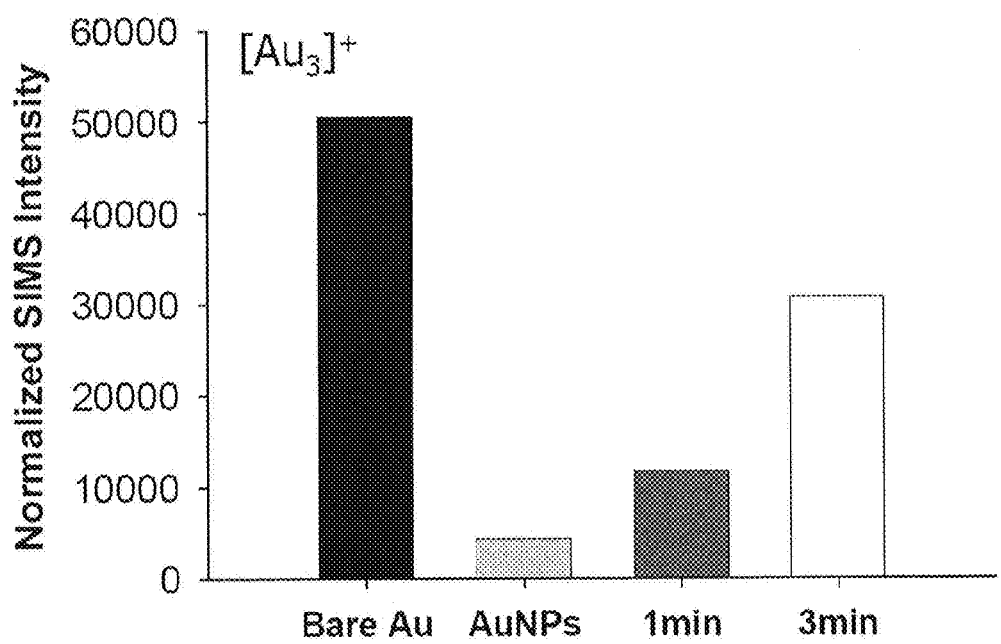
Figure 4D:
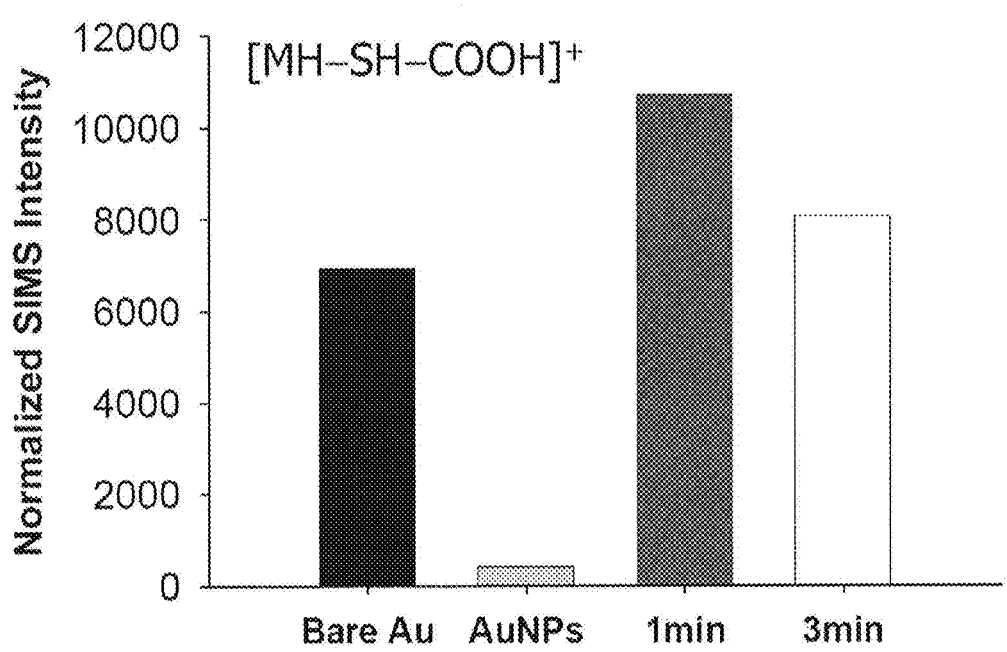

FIG. 4A to 4D show secondary ion mass spectrometry spectra with respect to the substrate on which the biochemical material is bonded, and FIG. 4A and FIG. 4C show results of $[Au_3]^+$ (m/z=591) and FIGS. 4B and 4D show results of $[MH-SH-COOH]^+$ (m/z=1085.61, M=1162.58) of peptide. Specifically, the results of FIG. 4A to 4D were obtained from a sample where peptide was bonded to a substrate by using 10 μM of an aqueous peptide solution.

In the measurement results set forth below, 'Bare Au' indicates results of a thin film substrate, 'AuNPs' indicates results of a nanoparticle substrate, '1 min' indicates results of a first core-shell particle substrate, and '3 min' indicates results of a second core-shell particle substrate.

It can be seen from FIG. 4A and FIG. 4C that, secondary ion (m/z) intensity of $[Au_3]^+$ exhibited the lowest intensity in the case where only nanoparticles were formed, and became higher in the order of the first core-shell particle substrate, the second core-shell particle substrate, and the thin film substrate, and, as the coverage of Au covering the surface became larger, Au ion intensity became higher.

Whereas, it can be seen from FIG. 4B and FIG. 4D that secondary ion intensity of peptide was the highest in the first core-shell particle substrate; higher in the second core-shell particle substrate than in the thin film substrate; and the lowest in the nanoparticle substrate.

It can be seen from the results of FIG. 4A to 4D that adsorption of peptide and intensity of peptide on the surface of the substrate were influenced by the surface coverage of Au on the substrate and the shape of three-dimensional Au particles. It can be seen that the shape of three-dimensional Au particles may influence adsorption density and ionized desorption efficiency of the biochemical material; a spherical shape or a cut spherical shape may be maintained in the case of a composite particle of the first core-shell particle substrate; and the specific surface of Au allowing adsorption of peptide is increased to provide the best intensity enhancing effect.

Although not shown in the drawings, in the case where the Si substrate to which gold nanoparticles were bonded was liquid-phase-reduced for 5 minutes, neighboring composite particles were contacted with each other while forming a grain boundary, to thereby manufacturing a film type sample. It can be confirmed that secondary ion mass spectrometry results of this sample were similar to results of thin film substrates in FIG. 4B and FIG. 4D An aqueous peptide solution containing peptide NRVYI-HPFHL (Mr=1294.69, angiotensin I peptide) (Peptron Co., Ltd., Korea), where thiol group strongly bonded to gold is not present, in a molar concentration of 10 μM, instead of peptide Ac-IYAAPKKGGGGC, was used to bond the peptide to the substrate.

Figure 5:
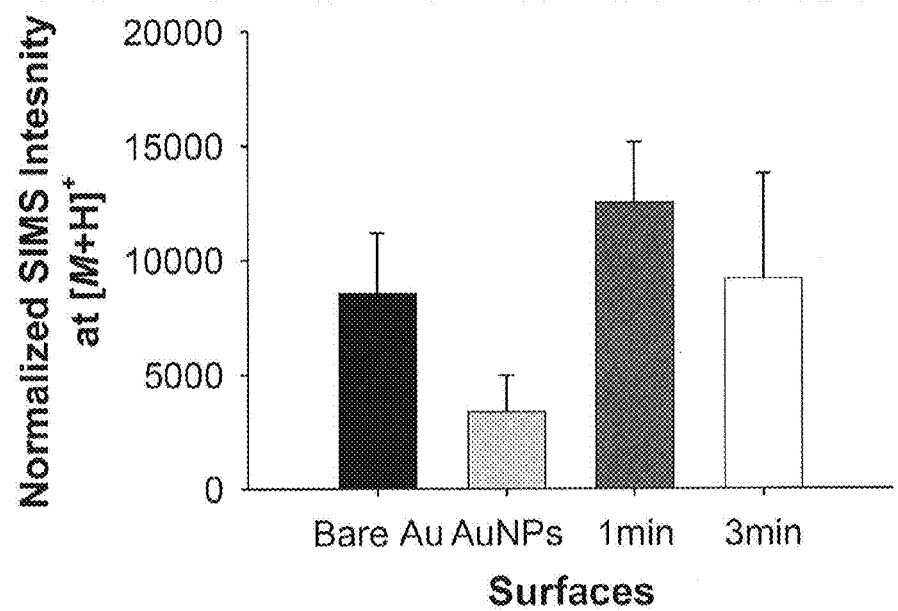
FIG. 5 shows secondary ion mass spectrometry spectra measurement results with respect to substrates to which peptide not containing a thiol group is bonded.

FIG. 5 shows secondary ion mass spectrometry spectra measurement results of substrates to which peptide NRVYI-HPFHL was immobilized. FIG. 5 shows results obtained by using $[M+H]^+$ (M=1294.69) peak as peptide analysis peak. It can be seen from FIG. 5, that unlike Cysteine-tethered Abl peptide performing bonding while having uniform directivity by strong bonding between Au and S, angiotensin I peptide performing bonding by mainly electrostatic adsorption or hydrophobic adsorption also had similar secondary ion spectra results to the Cysteine-tethered Abl peptide.

That is, it can be seen that amplification in secondary ion intensity was the best in the first core-shell particle substrate; secondary ion intensity of the second core-shell particle substrate was better than that of the thin film substrate; and secondary ion intensity was the lowest in the nanoparticle substrate.

Figure 6:
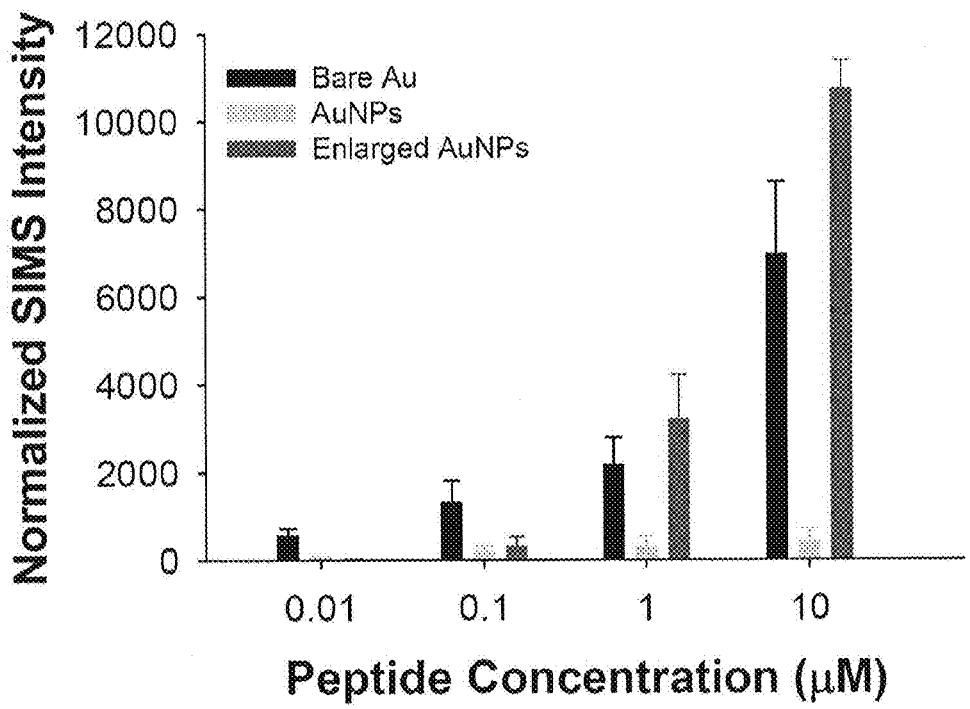
FIG. 6 shows secondary ion mass spectrometry spectra measurement results according to the peptide concentration in an aqueous peptide solution used to bond peptide to a substrate.

FIG. 6 shows secondary ion mass spectrometry spectra measurement results according to concentrations of the peptide in the aqueous peptide solution used in order to bond the peptide to the manufactured substrate. In FIG. 6, Enlarged AuNPs' means results of the first core-shell substrate. It can be seen from FIG. 6 that peptide secondary ion intensity was higher in the nanoparticle substrate than in the core-shell substrate for all concentration ranges. In addition, It can be seen that enhancement effect in secondary ion intensity of the core-shell substrate was best at concentrations of 1 μM or higher, but secondary ion intensity was better in the thin film substrate than in the core-shell substrate at concentrations of 0.1 μM or lower.

These results at low concentrations (0.1 μM or lower) may be interpreted to occur since, after the peptide bonded to Au surface is immobilized to the surface of the core-shell having a three dimensional structure, only the peptide present in an upper layer portion (1~2 nm) of the core-shell takes part in a reaction at the time of mass spectrometry. In the case of a flat surface of gold, most peptides take part in mass spectrometry signal when the same concentration of peptide was adsorbed to the surface of the flat gold, and thus, the signal tends to relatively increase. This is consistent with the results that the core-shell substrate had better secondary ion intensity than the thin film substrate in the case where the concentration of peptide in the aqueous peptide solution is high so that peptide is saturated on Au surface to which peptide is bondable within the same time period.

In the bio-chip according to the present invention, intensity of secondary ion mass signal is remarkably amplified, thereby accurately and precisely detecting a biochemical material without label, remarkably improving the accuracy in detection, detecting an infinitesimal amount of biochemical material due to significantly excellent signal to noise ratio (SNR), sensitively and accurately detecting a biochemical material having a very large mass, and allowing more stable and reproducible analysis.

What is claimed is:

1. A bio-chip for secondary ion mass spectrometry for analyzing a biochemical material using the secondary ion mass spectrometry, the bio-chip comprising:
    a substrate; and
    core-shell particles positioned above substrate,
    wherein the core-shell particles each include a metal nanoparticle as a core and a metal shell surrounding the metal nanoparticle.

2. The bio-chip of claim 1, wherein the metal shell of each of the core-shell particles is a metal layer formed by dipping a substrate on which metal nanoparticles are positioned in a metal ion solution containing metal ions, reducing the metal ions, and inducing nucleation and growth using the metal nanoparticles as a seed.

3. The bio-chip of claim 1, wherein the core-shell particles satisfy Relational Formula 1 below:

$$SCnp < SCcs < 1 \quad \text{(Relational Formula 1)}$$

(In Relational Formula 1, SCnp is surface coverage of metal nanoparticles on a surface of the substrate and means area of the substrate covered with the metal nanoparticles per unit surface area of the substrate; and SCcs is surface coverage of core-shell particles on the surface of the substrate and means area of the substrate covered with the core-shell particles per unit surface area of the substrate).

4. The bio-chip of claim 1, wherein the substrate is a composite substrate having a self-assembled monolayer formed on the surface of the substrate, and the metal nanoparticles are bonded with terminal groups of the self-assembled monolayer to thereby be immobilized onto the substrate.

5. The bio-chip of claim 4, wherein the substrate and the core-shell particle are surface-contacted with each other by the metal shell of the core-shell particle.

6. The bio-chip of claim 1, wherein the biochemical material as an analyte for mass spectrometry is bonded to the core-shell particle.

7. The bio-chip of claim 1, wherein a metal of the metal nanoparticle is Au or Ag, and a metal of the metal shell is Au or Ag.

8. A mass spectrometry method of a biochemical material for analyzing secondary ion mass of the biochemical material by using the bio-chip of claim 1 and secondary ion mass spectrometry.

9. A method of fabricating a bio-chip for secondary ion mass spectrometry for analyzing a biochemical material using the secondary ion mass spectrometry, the method comprising:
    a) positioning metal nanoparticles above a substrate; and
    b) forming core-shell particles each consisting of the metal nanoparticle as a core and a metal shell, by growing the metal shell, which is a metal layer surrounding a surface of the metal nanoparticle, using the metal nanoparticle as a seed through a liquid phase reduction method.

10. The method of claim 9, wherein step a) includes:
    a1) forming a self-assembled monolayer on a surface of the substrate; and
    a2) coating a dispersion liquid containing the metal nanoparticles on the substrate having the self-assembled monolayer formed thereon, to thereby bond terminal groups of the self-assembled monolayer and the metal nanoparticles with each other.

11. The method of claim 9, wherein step b) is performed by dipping the substrate on which the metal nanoparticles are positioned in a mixture solution containing metal ions and a reducing agent.

12. The method claim 11, wherein step b) includes:
    b1) dipping the substrate on which the metal nanoparticles are position in a metal ion solution containing metal ions; and
    b2) feeding a reducing agent into the metal ion solution to reduce the metal ions, to thereby form the metal shell as the metal layer surrounding the metal nanoparticle.

13. The method of claim 11, wherein the reducing agent is hydroxylamine hydrochloride, cetyltrimethylammonium bromide, nicotinamide adenine dinucleotide, or a mixture thereof.

14. The method of claim 11, wherein a size of the core-shell particle, a shape of the core-shell particle, and a distance between the core-shell particles are controlled by the time period while reducing in step b) is performed.

15. The method of claim 9, wherein at the time of the liquid phase reduction method, the molar concentration of metal ions in a liquid containing a metal ion solution is 0.1 to 10 mM, and a reducing agent reducing the metal ions is fed to have a molar concentration of 0.1 to 10 mM in the liquid.

16. The method of claim 9, further comprising, after step b), c) coating an analysis solution containing the biochemical material on a surface of the substrate on which the core-shell particles are formed, to thereby bond the biochemical material to the core-shell particles.

17. The method of claim 16, wherein the molar concentration of the biochemical material in the analysis solution is 0.01 to 10 μM.

* * * * *